Figure 1A:
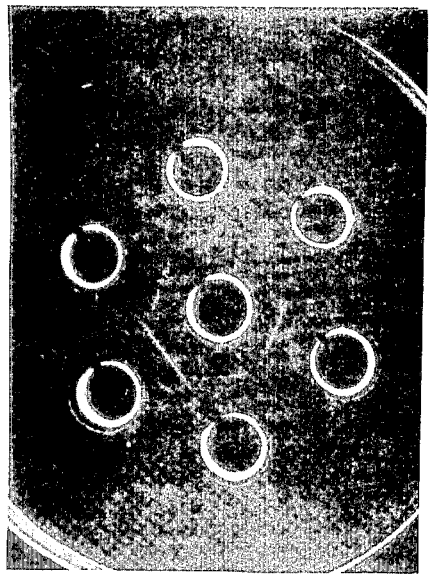
Figure 1A:
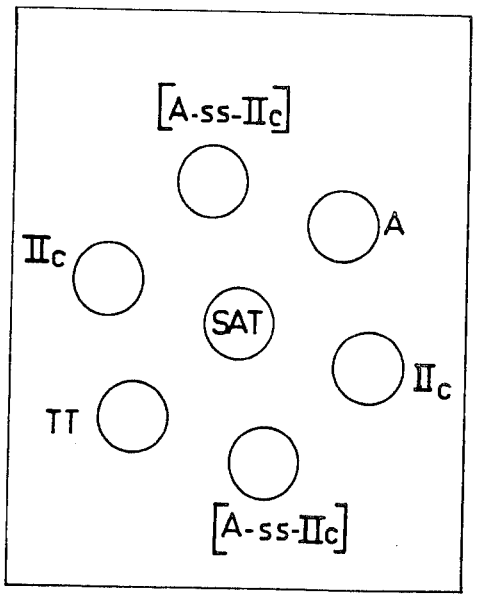
Figure 1B:
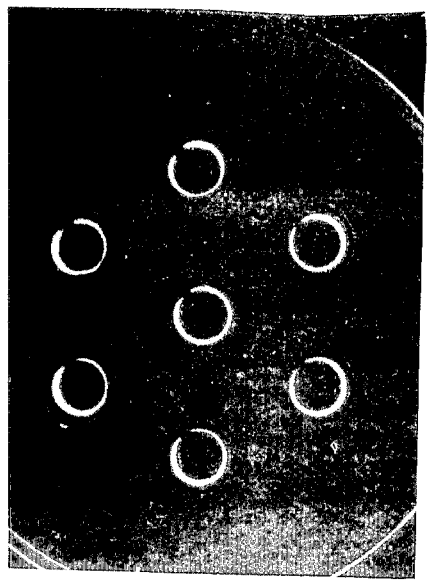
Figure 1B:
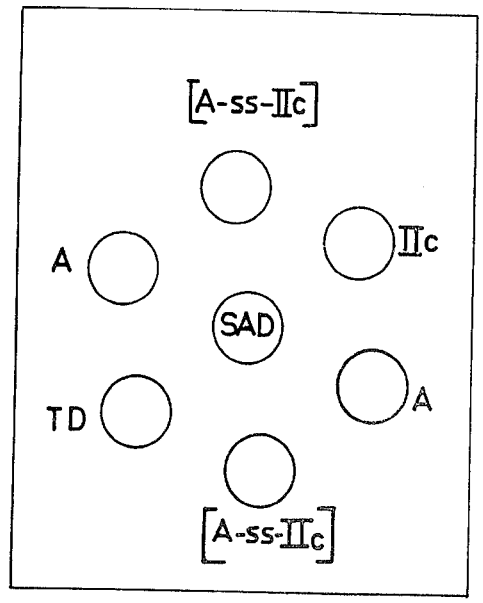

United States Patent [19]

Bizzini

[11] Patent Number: 4,479,940
[45] Date of Patent: Oct. 30, 1984

[54] THIOLATED POLYPEPTIDE COMPOUND DERIVED FROM A TETANUS TOXIN FRAGMENT, THE PROCESS FOR ITS OBTENTION AND ITS APPLICATIONS

[75] Inventor: Bernard Bizzini, Paris, France
[73] Assignee: Institut Pasteur, Paris, France
[21] Appl. No.: 341,335
[22] Filed: Jan. 21, 1982

[30] Foreign Application Priority Data

Jan. 22, 1981 [FR] France ............... 81 01176

[51] Int. Cl.³ ............... C07C 103/52; A61K 37/02
[52] U.S. Cl. .................. 424/177; 260/112.5 R; 260/112 R
[58] Field of Search ........ 260/112.5 R, 112 R; 424/177

[56] References Cited

U.S. PATENT DOCUMENTS

| 2,938,023 | 5/1960 | Weygand et al. ........... 260/112.5 R |
| 3,171,831 | 3/1965 | Town ......................... 260/112.5 R |
| 4,007,265 | 2/1977 | Helting . |
| 4,150,033 | 4/1979 | Kitagawa . |
| 4,284,624 | 8/1981 | Natarajan et al. ............ 424/177 |
| 4,315,031 | 2/1982 | Vincent et al. .............. 424/305 |

FOREIGN PATENT DOCUMENTS

| 2334954 | 7/1977 | France . |
| 2366569 | 4/1978 | France . |
| 2470773 | 6/1981 | France . |
| 1492445 | 11/1977 | United Kingdom . |
| 1586506 | 3/1981 | United Kingdom . |

OTHER PUBLICATIONS

*Chemical Abstracts,* vol. 93, No. 9, Sep. 1980, p. 111, Abstract No. 89284M.
Bizzini et al., *J. of Neurochemistry,* vol. 28, 1977, pp. 529–542.
*Chemical Abstracts,* vol. 93, No. 7, Aug. 1980, p. 254, Abstract No. 63204K.
King et al., *Biochemistry,* vol. 17, No. 8, 1978, pp. 1499–1506.
Morris et al., *J. of Biological Chem.,* vol. 255, No. 13, 1980, pp. 6071–6076.
Bizzini et al., *Brain Research,* 193, 1980, pp. 221–227.

*Primary Examiner*—Delbert R. Phillips
*Assistant Examiner*—F. T. Moezie
*Attorney, Agent, or Firm*—Frost & Jacobs

[57] ABSTRACT

A new thiolated polypeptide compound derived from a fragment of tetanus toxin, the process for its obtention and its applications.

This compound consists of the $II_c$ fragment of tetanus toxin, having at least one —SH group either directly or indirectly bound thereto. It is usable as a specific neuropharmacological transport agent for transporting a medicine to the central nervous system, as a specific labelling agent for neuronal cells or for diagnosis purposes. It can be coupled with a medicine or a labelling agent.

6 Claims, 5 Drawing Figures

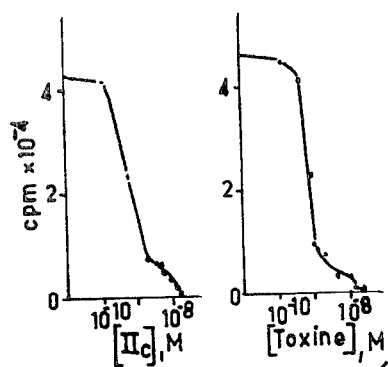
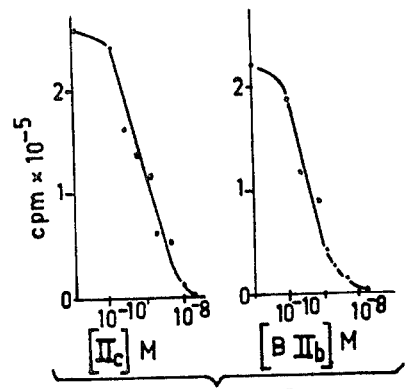
FIG.2A  FIG.2B
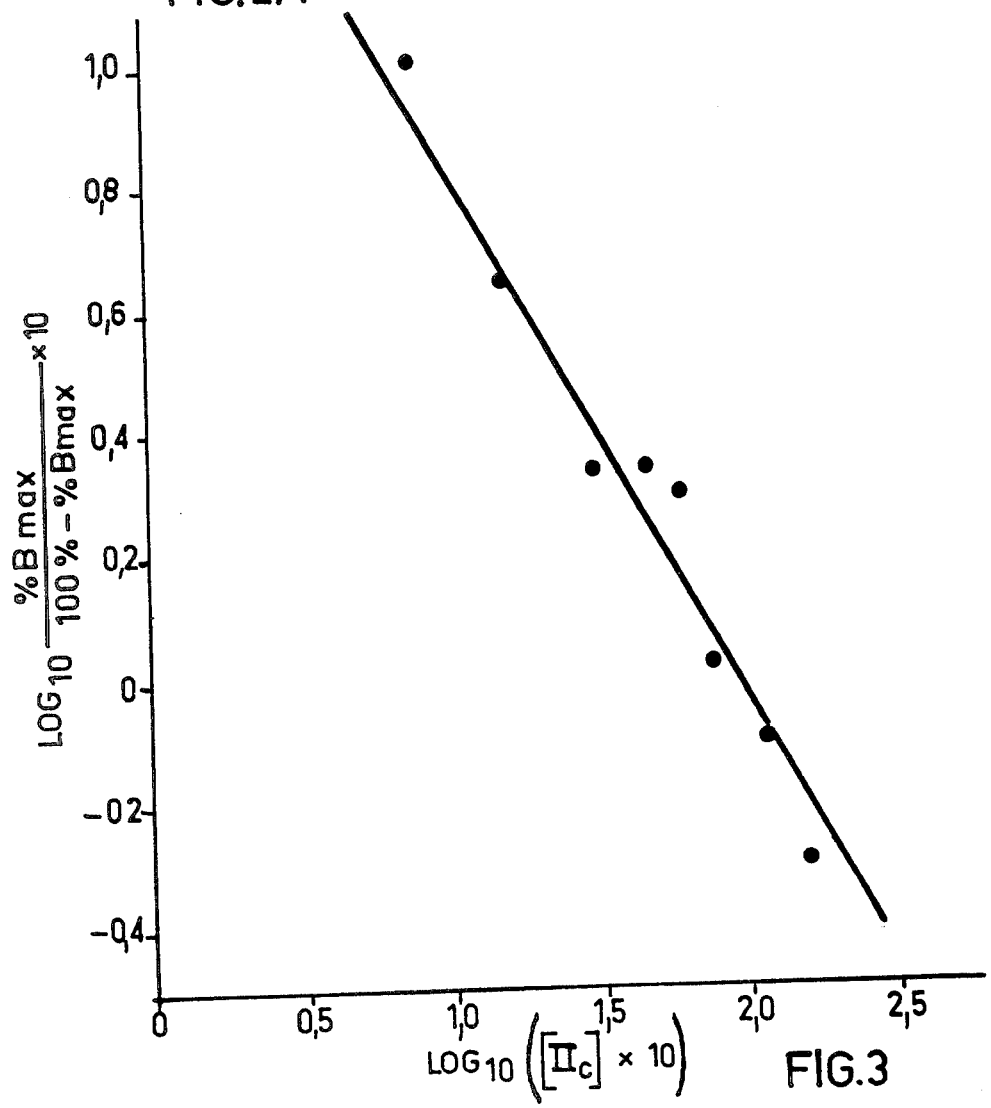
FIG.3

THIOLATED POLYPEPTIDE COMPOUND DERIVED FROM A TETANUS TOXIN FRAGMENT, THE PROCESS FOR ITS OBTENTION AND ITS APPLICATIONS

The present invention relates to a new thiolated polypeptide compound derived from a tetanus toxin fragment, to the process for its obtention and its applications.

With regard to the tetanus toxin itself or its anatoxin, it was already proposed to use them notably for obtaining vaccines or assay reagents. In order to illustrate this prior art following references will be cited:

FR patent for addition No. 74,16,936 published under No. 2,270,891, which relates to a process for obtaining vaccines by treatment of a toxic product with glutaraldehyde. This process consists in treating a toxic product with glutaraldehyde in effecting the polymerisation of a limited number of molecules of said product and the detoxification of said product. In this process tetanus toxin may be used as toxic product.

FR patent application No. 77,29,186, published under No. 2,366,569, relates to an immunochemical process for assaying haptens, wherein are used a particle sensitized by an antibody, prepared by sensitizing fine particles by an antibody of the hapten to be assayed and a hapten-carrier conjugate. The carrier of this conjugate may be notably tetanus toxoid.

This hapten-carrier conjugate is used as reagent in an immunochemical process and also for immunization of an animal in order to obtain corresponding antibodies [see on page 4, lines 20 to 32].

The tetanus toxoid is therefore used as a carrier of the hapten in the body of the animal for obtaining antibodies. However, there exists no teaching in this FR patent about a particular fragment of tetanus toxin and its possible use as axonal transport agent for drugs.

GB patent No. 2,013,690 relates to an antigen for early pregnancy test and contraceptive vaccine. This antigen is obtained from the β-subunit of human chorionic gonadotrophin by reducing and cleaving of three, four, five or six of intrachain disulphide bounds of said β-subunit, alkylating of the thus reducing intrachain disulphide groups and isolating of the produced antigen. This antigen may be coupled with a protein or a hapten to enhance its immunological specificity. Tetanus toxoid is cited as suitable protein.

GB patent No. 1,492,445 relates to a composition comprising a conjugate of a subject-compatible immunogenic carrier and an immunochemically purified hormone derivative. The tetanus toxoid is used as carrier in this composition.

DE-OS patent application No. 1,617,880 relates to a process for obtaining bioactive organotrope substances, particularly drugs. This process consists in making a conjugate of a biologically active substance with organotrope receptive substances obtained from cellular membranes or antibodies. The toxins may be used as organotrope substances.

Furthermore, it was proposed to use thiolated proteins as drug carriers. Reference may be made to U.S. Pat. No. 3,171,831 which relates to thiolation of proteins by reaction with homocysteine thiolactone in the presence of a tertiary amine. The thiolated proteins thus obtained, for example gelatin, may be used as carriers for drugs. According to example 18 of this U.S. Pat. No. 3,171,831 the gelatin thus treated is used for encapsulating a pharmaceutical product which is sensitive to the acid environment of the stomach. The pharmaceutical product is therefore in this case not coupled with the thiolated protein but coated with it.

On the other hand, it was disclosed in FR patent application No. 76,37,367 published under No. 2,334,954 a reagent for immunoenzymatic determination. This reagent is composed by an antigen and an enzyme coupled by means of an ester of maleimidobenzoic acid and n-hydroxy-succinimide.

It is known that tetanus toxin is retrogradely transported to the central nervous system and the peripheral nervous system. In this respect, reference may be made to the article of BIZZINI et al entitled: "An antigenic polypeptide fragment isolated from tetanus toxin:- chemical characterization, binding to gangliosides and retrograde axonal transport in various neuron sytems", which appeared in the "Journal of Neurochemistry", 1977, vol. 28, pp 529–542, and to all the bibliographic references cited in this article.

Various studies have shown that tetanus toxin may be degraded or cleaved into several fractions or subunits. For example, COHEN et al [The Journal of Immunology vol. 104, No. 6 June 1970] have shown that the freezing-thawing of the crude filtrate of *Clostridium tetani* culture results in a degradation of the molecule of tetanus toxin; the resulting degraded tetanus toxin is practically devoid of toxicity and has a flocculating power lower than the one of tetanus toxin.

BIZZINI and RAYNAUD have also studied the subunits A-I, A-II, A-III and B-I, B-II and B-III of tetanus toxin. [C.R. Acd. Sc. Paris, T.279,1974 series D, pp. 1809–1811 and Annales of Pasteur Institute Paris 126, 159–176 (1975)]. French patent No. 74,36,622 (publication No. 2,249,679) discloses an immunogenic atoxic product obtained from tetanus toxin. This atoxic product is obtained by the treatment of tetanus toxin with a proteinase.

MORRIS et al. in the Journal of Biological Chemistry vol. 255 No. 13 July 10, 1980 pp. 6071–6076 disclose the interaction of fragments B and C of Tetanus toxin with neural and thyroid membranes and with gangliosides. It is notably noted in this article that fragment C, obtained by papain digestion at 55° C., undergoes retrograde transport in a manner similar to that of intact tetanus toxin, whereas fragment B does not similarly accumulate in the first distal segment to the ligation but does appear to be taken up or internalized in a diffuse patern (see on page 6075, left column).

The principal physico-chemical properties of the different subproducts of tetanus toxin are given on page 230 of article entitled "Tetanus toxin" of BIZZINI in Microbiological Reviews, June 1979, p. 224-240 and notably those of fragment C and fragment II$_c$ which is obtained, by papain digestion at a temperature at which no formation of fragment C occurs.

BIZZINI et al have also isolated from frozen crude toxin a polypeptide fragment of the toxin which is identical, from the immunological point of view, to the above mentioned fragments A-II and B-II, but differs therefrom by its size and toxicity [see in this respect Journal of Neurochemistry, 1977, vol. 28, pp. 529–542]. This fragment, named B-II$_b$, is capable of binding to the gangliosides and to the synaptic membranes with an affinity which is even greater than that of tetanus toxin.

French patent application No. 79,29,289, discloses a new thiolated peptide compound derived from tetanus toxin, the process for its obtention, and its applications.

This thiolated polypeptide compound consists of the B-II$_b$ fragment of tetanus toxin having bound thereto at least one —SH group; this compound substantially exhibits the same properties of axonal retrograde transport and of binding to the tetanus toxin receptors as the B-II$_b$ fragment itself. This thiolated polypeptide compound is suitable as a neuropharmacological transport agent for conducting to the central nervous system pharmacological or chemotherapeutic agents. This polypeptide agent is also suitable as a labelling agent for neuronal cells. The properties of this thiolated polypeptide compound are also described in Brain Research 193 (1980) 221–227.

There has been now found a new thiolated polypeptide compound derived from another tetanus toxin fragment, which may be also used as a neuropharmacological transport agent to transport pharmacological or chemotherapeutic agents to the central nervous system.

The present invention therefore relates to a new thiolated polypeptide compound, its obtention and its applications.

The thiolated polypeptide compound according to the invention is the $II_c$ fragment of tetanus toxin having bound thereto at least one —SH group and substantially exhibiting the same properties of axonal retrograde transport and of binding to the tetanus toxin receptors as the $II_c$ fragment itself.

The B-$II_b$ fragment of tetanus toxin is derived from a frozen filtrate of a culture of *Clostridium tetani* (Harvard strain No. 6037 of Collection Nationale de Cultures de Microorganismes de l'Institut Pasteur in PARIS, FRANCE) by ultrafiltration for removing the substances with a molecular weight lower than 10,000, then by fractionating by means of ammonium sulfate and gel filtration.

A number of fragments similar to the B-$II_b$ fragment may be obtained by papain digestion of the whole tetanus toxin or of the heavy chain thereof (beta fragment). In this connection, reference may be made to the following articles:

BIZZINI, B. and RAYNAUD, M. entitled "Immunological and biological study of subunits of tetanus toxin" *C.R. Acad. Sci.* (*Paris*), 279, series D (1974) 1809–1812.

BIZZINI, B., International Symposium or Venoms and Toxins, March 4–6, 1977, Bombay (India); abstract published in Toxicon (1978), volume 15, p. 141.

BIZZINI B., Tetaus toxin *Microbiol. Rev.* 43 (1979) 224–240.

The $II_c$ fragment is obtained by digestion of the purified tetanus toxin by means of papain insolubilized on the gel, "Sepharose 4B", activated with cyanogen bromide according to the procedure disclosed in the previously mentioned Compte Rendu de l'Académie des Sciences [T.279 December 1974; series D-1809], except that digestion is effected only for 4 hours.

Statement will be given hereinafter of the procedure to obtain the $II_c$ fragment used as a starting compound for providing the polypeptide compound according to the invention. There was used the purified tetanus toxin derived from a filtrate of a 5-day culture of *Clostridium tetani* obtained by the process disclosed by:

BIZZINI, B. TURPIN A., and RAYNAUD, M. in the article entitled Production and purification of the tetanus toxin *Ann. Institut Pasteur, Paris* 116 (1969) 686–712.

The purified tetanus toxin thus obtained assayed 3150 $L_f$(Limes floculationis or Floculation unit) per mg of N and 1,2.$10^8$ MLD (Minimum lethal dose) per mg of N.

120 mg of the purified tetanus toxin were treated for 4 hours at 37° C. in a water bath, with 200 units of inslublized papain, under occasional stirring.

At the end of the digestion period, the papain was immediately removed by centrifugation for 5 minutes at 10,000×g in a centrifugal machine refrigerated to 4° C.

The supernatent was filtrated on a column of "Sephadex G-100" (2.5×80 cm) buffered with 0.1 M tris, HCl buffer, pH 8, containing 1 M of NaCl. The effluent was continuously controlled at 280 nm and collected in 2 ml-fractions. The fractions corresponding to the peak, having a molecular weight close to 45,000, were combined together. The volume of the combined fractions was reduced to 2 ml before filtration on a column (2.5×80 cm) of polyacrylamide-agarose gel known under the trade name "Ultrogel AcA 54", using the same buffer. The fractions representing the main peak were combined together and the resulting volume was reduced to 3 ml by dialysis against a solution containing 50% of polyethylene glycol 20,000 (sigma).

The undigested toxin or the $I_{bc}$ fragment liable to contaminate the $II_c$ fragment were adsorbed on an affinity column of "Sepharose" gel activated with cyanogen bromide which previously had coupled thereto, covalently, the IgG fraction of an anti-$I_{bc}$ serum. The unadsorbed fraction present in the filtrate constitutes the $II_c$ fragment. This fragment is not toxic to mice at a dose of 1 mg at one time.

The affinity column was prepared according to the following procedure. The IgG fraction was isolated by precipitating the anti-$I_{bc}$ fragment antiserum. The anti-fragment $I_g$G fraction assayed 1,500 $L_f$per ml. The IgG fraction was coupld to "Sepharose 4B" activated with cyanogen bromide according to the procedure disclosed by Wilchek et al. "A general method for the specific isolation of peptides containing modified residues, using insoluble antibody columns. *Biochemistry* 10 (1971) 2828–2834."

The $II_c$ fragment has the following physicochemical properties:

molecular weight of about 46,000 it
interacts with gangliosides
it is free of toxicity
it interacts with synaptic membranes isolated from rat spinal cord.

The immunological properties of the $II_c$ fragment are as follows:

the $II_c$ fragment rise to a cross reaction with the tetanus toxin and the heavy chain ($\beta$ fragment) thereof, The $II_c$ fragment gives rise to an identity reaction with the B-$II_b$ fragment; the $II_c$ fragment gives rises to a non-identity reaction with the $I_{bc}$ fragment and the light chain ($\alpha$ fragment).

The main characteristics of the $II_c$ fragment are summarized in the articles by B. BIZZINI (Microbiological Reviews, June 1979, pp. 224–240 and Toxicon (1978), Vol. 15, p. 141) wherein it is stated that the fragments similar to the B-$II_b$ fragment may be obtained by digestion by means of papain and that those fragments probably contain the portion of the heavy chain which is involved in the binding of the toxin molecule to its receptors in the nervous cell. On the other hand, it is stated that the tetanus toxin fragments, which still have the ability to bind with gangliosides should undergo axonal retrograde transport as the whole toxin does.

It was now found that the II$_c$ fragment may be bound to synaptic membranes and could undergo axonal retrograde transport to the central nervous system. The thiolated II$_c$ fragment, which is the object of the present invention, will also undergo axonal retrograde transport to the central nervous system and will bind to the synaptic membranes. Since in this field any chemical modification might inhibit the pharmacological properties of a fragment, it was not at all obvious, even in view of the teachings relating to the B-II$_b$ fragment, that the thiolated polypeptide compound according to the invention could also be used as an axonal retrograde carrier for pharmacological or chemotherapeutic agents or as a diagnosis reagent, either alone or as associated with another substance adapted to evidence, for example, a specific antigen in the central nervous system.

The present invention therefore relates to a new thiolated polypeptide compound consisting of the II$_c$ fragment bearing at least one —SH group, suitable especially as a neuropharmacological transport agent and as a specific labelling agent for neuronal cells.

Similarly to the process for obtaining the thiolated polypeptide compound according to FR patent No. 79,29,289, the —SH group or groups is or are directly or indirectly bound to the II$_c$ fragment. In general, taking into account the process for its obtention, which involves a thiolation, the binding of the —SH groups will occur through the residue of the thiolation agent. Besides, the latter is bound to the II$_c$ fragment through the —NH$_2$ groups carried thereby.

The thiolated polypeptide compound according to the present invention is produced by thiolation of the II$_c$ fragment obtained by the above described process.

The thiolation of the II$_c$ fragment can be carried out by conventional means permitting the introduction of —SH groups on a molecule comprising amino groups, but for the purposes of the invention, the means in question should not denature the properties of axonal transport and of binding to the specific receptors of the tetanus toxin in the central nervous system, of the II$_c$ fragment.

By way of example, it will be mentioned that the thiolation of the II$_c$ fragment can be achieved with the following thiolation agents:

4-methyl-mercaptobutyrimidate:

$$HS-(CH_2)_3-\underset{\underset{NH_2^+Cl^-}{\|}}{C}-CH_3$$

(Biochemistry vol. 17 No. 8, 1978)

2-iminothiolane (Schramm H. J. and Dölffer T. (1977) Z. Physiol. Chem. 358; 137–139).

N-acetylhomocysteine thiolactone (AHT) (see J. Am. Chem. Soc. 1960, 82, 565–571)

$$\begin{array}{c} \quad\quad S \\ \quad\diagup \;\; \diagdown \\ H_2C \quad\quad C{=}O \\ | \quad\quad\quad | \\ H_2C{-\!\!-\!\!-}CH \\ \quad\quad | \\ \quad\quad NHCOCH_3 \end{array}$$

S-acetyl-mercaptosuccinic anhydride (AMS) (J.Am.Chem. Soc.1959,81, 3802–3803)

$$CH_3-CO-S-CH-C\underset{\underset{O}{\diagdown}}{\overset{\overset{O}{\diagup\!\!\!\!\!/}}{\phantom{x}}}$$
$$\phantom{CH_3-CO-S-}| \phantom{--} O$$
$$\phantom{CH_3-CO-S-}CH_2-C\underset{\diagdown\!\!\!\!\diagdown}{\diagup}$$
$$\phantom{CH_3-CO-S-CH_2-C-}O$$

On the other hand, it will be mentioned that the known processes of thiolation consisting of a dithiopyridylation step and a reduction step are unsuitable for the purposes of the invention. Indeed, the properties of axonal transport and of binding of the thus thiolated II$_c$ fragment are modified in the course of the reduction step.

For example, the thiolation effected by reaction with the N-succinimidyl-3-(2-pyridyl-dithio)-propionate and by reduction of the dithiopyridylated compound so obtained, for example according to the procedure described by CARLSSON et al [Bioch, J. (1978) 173 723–724] is unsuitable for the purposes of the invention.

In order to be more precise, it will be stated that the thiolated polypeptide compound according to the invention comprises one or more Z—SH groups, in which Z is the residue of the thiolation agent.

Thus, if one of the thiolation agents mentioned above is employed, Z then represents:

$$-\underset{\underset{}{\overset{\overset{NH_2^+,\,Cl^-}{\|}}{C}}}{\phantom{x}}-(CH_2)_3-;\; -CO-\underset{\underset{NH-CO-CH_3}{|}}{CH}-CH_2-CH_2-;\; -\underset{\underset{CH_2-COOH}{|}}{CH}-CO-;$$

$$-\underset{\underset{NH}{\|}}{C}-(CH_2)_3-$$

The thiolation of the II$_c$ fragment is achieved on the NH$_2$ groups thereof.

It has been found that the thiolated polypeptide compound according to the invention is suitable as a neuropharmacological transport agent for transporting pharmacological or chemotherapeutic agents to the central nervous system.

In order to allow the transport of a medicine to the central nervous system by means of the agent according to the invention, this medicine must be bound to the thiolated polypeptide compound, employed as a transport agent, without of course modifiying the pharmacological property of the medicine or the property of the II$_c$ fragment to be bound to the specific receptors of the tetanus toxin in the central nervous system. The term "Medicines" is intended to designate, according to the invention, any substances having pharmacological properties, such as pharmacological agents, chemotherapeutic agents and the like. The medicines which may be bound according to the invention to the polypeptide compound employed as a neuropharmacological transport agent must have —NH$_2$ groups.

As examples of medicines which may be transported to the central nervous system by means of the thiolated polypeptide compound according to the invention, there may be mentioned: alkaline phosphatase, the A fragment of cholera toxin, the A fragment of diphtheria toxin, dipyrido-indoles according to French patent No. 77,11,148 and generally, any medicine having —NH$_2$ groups.

It is known that the cholera toxin is bound to the GM₁ gangliosides of the intestine wall and that the A fragment is responsible for the increase in the cyclic AMP rate (cyclic adenosine-monophosphoric acid). On the other hand, in tetanus a decrease in the cyclic AMP proportion in the central nervous system is found. The conjugate according to the invention, formed by the thiolated polypeptide compound coupled to the A fragment may be employed for controlling tetanus.

The dipyrido-indoles according to French patent No. 77,11,148 are chemotherapeutic agents of utility in the treatment of cancers. In this field, it is known that metastases are due to the fact that the cancerous cells come to nestle in the central nervous system hence they migrate to other regions of the body, where they develop tumors.

The development of metastases could be avoided or reduced provided that the means for destroying these cells in the central nervous system can reach the central nervous system.

In the same way, the invention may be applied to the treatment of cerebral tumors.

The present invention consequently also relates to the means for coupling the thiolated polypeptide compound according to the invention to medicines.

The means for coupling the compound according to the invention and the medicine to be transported use at least one disulphide bridge or at least one sulfur irreversible link.

The present invention therefore also relates to II$_c$ fragment medicine conjugates comprising at least one disulphide bridge or at least one sulfur irreversible link.

It is known to prepare protien conjugates by formation of an intermolecular disulphide bridge. The formation of such an intermolecular disulphide bridge is achieved for example by reaction of a protein having thiol groups with a protein having dithiopyridyl groups.

For example, according to the process described by TE PIAO KING et al [Biochemistry vol. 17 No. 8, 1978], two different proteins may be coupled by first binding thiol groups to one of the proteins and 4-dithiopyridyl groups to the other protein and by reacting the resulting modified proteins under suitable conditions in order to form a disulphide bridge and to eliminate 4-thiopyridone. The thiol groups may be bound to one of the proteins by means of 4-methyl-mercapto-butyrimidate and the 4-dithiopyridyl groups to the other protein by means of, for example, 3-methyl-(4'-dithiopyridyl)propionimidate. This coupling process produces a protein-protein conjugate in which the fraction between the two proteins is symmetrical with respect to the disulphide bridge.

According to CARLSSON et al. (Bioch. J., 1978, 173, 723-724) the thiol group can be introduced in one of the proteins by reaction of said protein with N-succinimidyl-3-(2-pyridyl-dithio)propionate and subsequent reduction; according to this process, the same reagent, namely the N-succinimidyl-3-(2-pyridyl-dithio)propionate, is used for introducing both thiol and dithiopyridyl groups in the proteins. The resulting conjugates also have a binding fraction which is symmetrical relative to the disulphide bridge.

4-methyl-mercapto-butyrimidate has also been used for forming higher dimers and oligomers of proteins of 30 S ribosome of *Escherichia Coli* (Biochemistry, 12, 3266–3273, 1973).

The conjugates thus obtained have many applications, for example as immunological assay reagents.

The process according to the invention for coupling the thiolated polypeptide compound used as a neuropharmacological transfer agent with a medicine by means of disulphide bridges comprises the steps of
(1)-introducing dithiopyridyl groups in the medicine to be bound;
(2)-reacting the medicine having the dithiopyridyl groups with the thiolated polypeptide compound according to the invention.

The reaction diagram of this coupling process may be represented in the following manner when the dithiopyridylation agent used in step 1 is N-succinimidyl-3-(2-pyridyl-dithio)propionate:

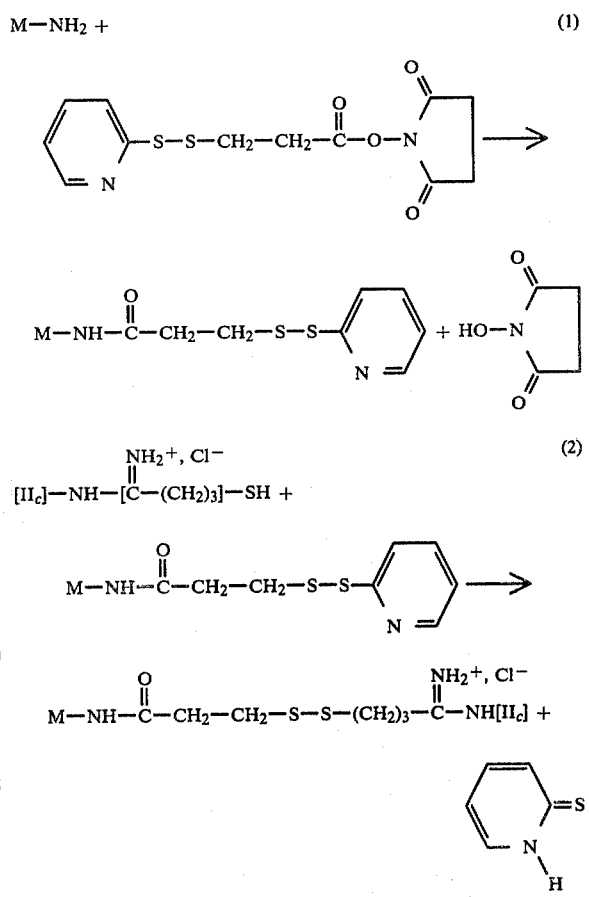

In this process, another dithiopyridylation agent may be employed, such as dithiopyridine or any other agent suitable for such a reaction.

Another way of coupling the polypeptide compound, used as a neuropharmacological transport agent according to the invention consists of creating an irreversible link between said agent and the medicine to be transported. This process may be represented by the following reaction diagram:

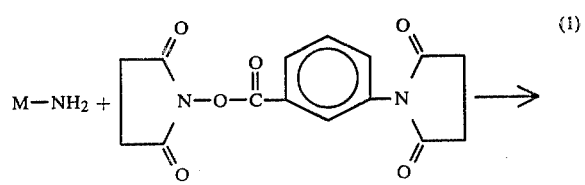

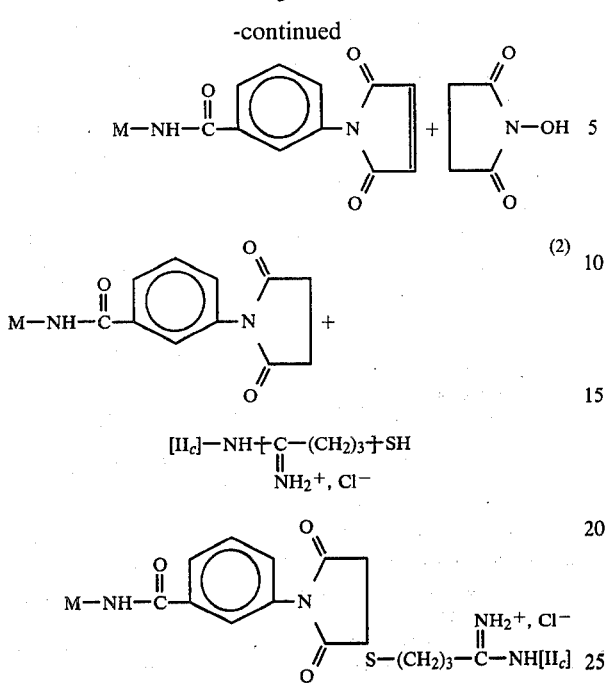

It comprises the steps of:
(1) reacting the medicine to be bound with the ester of methamaleimidobenzoyl-N-hydroxy-succinimide;
(2) reacting the resulting compound with the polypeptide compound according to the invention.

The foregoing reaction diagrams and those which will be given hereinafter are simplified and do not take into account the number of SH groups which may be bound to the $II_c$ fragment.

It was already proposed to use the ester of methamaleimidobenzoyl-N-hydroxy-succinimide for forming enzyme-antibody conjugates (FEBS Letters, vol. 95, No. 2, November 1978). However, the teachings of the prior art did not permit to foresee that the use of the ester of metamaleimidobenzoyl-N-hydroxy-succinimide for coupling the neuropharmacological transport agent according to medicines would not modify or inhibit the pharmacological properties of said medicine and the property of the $II_c$ fragment to be found to the specific receptors of the tetanus toxin in the central nervous system.

It will be observed that the coupling according to the invention of the medicine to the thiolated polypeptide compound employed as a neuropharmacological transport agent is achieved by known conventional techniques of protein-protein coupling. However, it should be noted that not all of the protein-protein coupling processes available to one skilled in the art are suitable for the purposes of the invention. Indeed, only the coupling processes which achieve a disulphide bridge or a sulfur irreversible link are suitable. In particular, it will be mentioned that the most conventional coupling process, which employs glutaraldehyde, is unsuitable for the purposes of the invention, since the $II_c$ fragment treated with glutaraldehyde loses its properties of axonal transport and of binding to the receptors of the tetanus toxin in the central nervous system. Thus, the $II_c$ fragment to which carbonyl groups would have been bound, for example with glutaraldehyde, is unsuitable for the purposes of the invention.

Another application of the thiolated polypeptide compound according to the invention, is the labelling of neuronal cells. Thus, the compound of the invention may be employed as a specific labeller of neuronal cells. It is also suitable for preparing immunological reagents. For example an enzymatic reagent may be preparedc from the thiolated polypeptide compound according to the invention and alkaline phosphatase. It was found that the resulting conjugate had both binding power of the $II_c$ fragment and the enzymatic activity of the phosphatase. The compound according to the invention is also suitable as a retrograde transsynaptic tracer.

The polypeptide compound of the invention is also appropriate to prepare a diagnosis reagent by coupling with a labelling molecule, such as an antibody, for example a radioactive antibody.

The invention will be now described in more detail by means of the examples illustrating the preparation of the thiolated polypeptide compound of the invention and the coupling of the latter with medicines. In all the examples, use was made of the $II_c$ fragment as defined hereinbefore.

EXAMPLE 1

Thiolation of the $II_c$ fragment by means of 2-iminothiolane

Thiolation of the $II_c$ fragment was achieved by means of the method described by Schramm et al. [Z. Physiol.-Chem. 1977, 358; 137–139].

The $II_c$ fragment (1.5 mg) in solution in 50% glycerol (0.2 ml) was thiolated by iminothiolane (2.5 mg) in solution in 750 μl of 0.2 M triethanolamine HCl buffer, pH 8.5–9.0. The reaction mixture was maintained at room temperature for 2 hours. The excess of reagent was eliminated by filtration on a "SEPHADEX G-25" column. The thiolated polypeptide product so obtained contained 2.7-SH groups.

EXAMPLE 2

Thiolation of the $II_c$ fragment by means of N-acetylhomocysteine thiolactone The $II_c$ fragment thiolation was effected by the procedure described by SINGER et al. [J. Am. Chem. Soc., 1960 82, 567–571[.

To 4 mg of the $II_c$ fragment in solution in 0.2 ml of water, there was added the $K_2CO_3/NaHCO_3$ buffer, pH 10.7 (0.2 ml). A nitrogen current was passed therethrough in order to expel the air. 0.2 ml of an 80 mg/l solution of N-acetylhomocysteine thiolactone was added. The reaction mixture was maintained for two hours at 4° C. under nitrogen. The reaction was thereafter stoppd by filtration on SEPHADEX G-25. The thus obtained product contained 4-SH groups.

EXAMPLE 3

Preparation of a conjugate of thiolated polypeptide compound /A fragment of the diphteria toxin 5 mg of the A fragment of diphteria toxin were used in 1.5 ml of 0.1 M phosphate buffer containing 0.5 M NaCl (pH 7.5). There was added 312 μg of N-succinimidyl-3-(2-pyridyldithio)propionate (Pharmacia) dissolved in 25 μl of 99.5% ethanol (Merck). After reacting for 30 minutes in a water bath at 23° C., the dithiopyridylated toxin was separated from the excess of reagent by filtration on "Sephadex G 25" buffered with the same buffer.

This procedure achieved introduction of 1.7 2-pyridyldisulphide grouping per mole of A fragment.

The $II_c$ fragment was thiolated by reaction with 4-methyl-mercaptobutyrimidate according to the method described by TE PIAO KING et al. (Biochemistry, vol. 17, No. 8, 1978), 5.37 mg of $II_c$ dissolved in 1.5 ml of 0.025 M borate buffer, pH 9.0, were reacted with 3 mg of the thiolation agent dissolved in 100 μl of methanol at 0° C. for 30 minutes. The excess of reagent was removed by filtration on "Sephadex G 25" balanced with a 0.1 M phosphate buffer, pH 7.0, containing 1 mM $Na_2$ EDTA. The thiolated $II_c$ fragment contained 2.5-SH groups per mole.

The conjugate was obtained by mixing 119 nanomoles of dithiopyridylated A fragment with 90.9 nanomoles of thiolated $II_c$ fragment. The exchange reaction was followed at 343 nm. Filtration was effected on "Sepharose 6B" buffered with a buffer Tris 0.05 M, 0.5 M NaCl, pH 8.0.

The conjugate thus obtained preserves the binding power of the $II_c$ fragment and the immunological reactivity of the A fragment and of the $II_c$ fragment.

FIGS. 1A and 1B illustrate the synthesis of the $II_c$-polypeptide conjugate. They represent the result of two gel immunodiffusion experiments.

The photograph in the left part of FIG. 1A shows the specific immunological reaction between the TT (tetanus toxin)fragment and the antitetanus serum disposed in the central well. No reaction occurs with the A fragment of the diphteria toxin. The A fragment of the diphteria toxin, which has an antigenic structure different from that of the tetanus toxin, exhibits no precipitation line when contacted with antitetanus serum.

In FIG. 1A, the [A-SS-$II_c$-] compound, viz. the thiolated $II_c$ previously coupled with the A fragment of diphterial toxin, is reacting with the antitetanus serum (ATS) through its tetanus antigenic determinants.

In FIG. 1B, the [A-SS-$II_c$-] compound is reacting with antidiphtheria serum (ADS) through the antigenic determinants borne by the A fragment of the diphterial toxin.

Thus, the photographs in FIGS. 1A and 1B show that synthesis of A-SS-$II_c$ conjugate occurred and that the two components, viz. the A fragment and the $II_c$ fragment, retained their antigenic properties after the coupling.

EXAMPLE 4

Pharmacological experiments

In these experiments, the $II_c$ fragment, the thiolated polypeptide compound according to the invention, as well as the tetanic toxin and the other fragments used for comparison purposes, such as fragment B-$II_b$, were labelled with 125 iodine. This labelling with 125 iodine was made according to the method of GREENWOOD et al. [The preparation of $^{125}$I-labelled human growth hormone of high specific radioactivity. *Biochem. J.* 89, (1963) 114–127].

The specific radioactivity of the $^{125}$I-labelled $II_c$ fragment used in the retrograde transport experiments was of 4 μCi per μg of protein. The $II_c$ fragment used for testing the binding to synaptic membranes had a specific radioactivity of 1.2 μCi per μg of protein. The specific radioactivity of the tetanic toxin was of 2.5 μCi per μg of protein.

(A)$II_c$ fragment binding to crude synaptic membranes

The crude synaptic membranes were prepared from the spinal cord of male Sprague Dawley rats of a weight of 150–200 g according to the Young and Snyder method, Strychnine binding associated with glycine receptors of the central nervous system. *Proc. Nat. Acad. Sci.* U.S.A. 70, (1973) 2832–2836. The protein concentration in the membrane suspension was adjusted to 1.0 mg per ml. The suspension was stored in aliquots of 1 ml at −25° C. The tests were effected according to the above-mentioned Young and Snyder method. The $II_c$, B-$II_b$ fragments, or the toxin, were caused to react with aliquots of 0.1 mg of crude synaptic membranes for 15 minutes at 21° C. in 1 ml of 0.05 M Na/K phosphate buffer, pH 7.4, containing 0.01% of "Triton X-100" The reaction was terminated by centrifuging during 10 minutes at 48,000×g and 4° C. The supernatent fluid was decanted and the sediment was washed three times with 5 ml of 0.05 M Na/K phosphate buffer, pH 7.4, containing 0.01% of "Triton X-100" and 0.1% of bovine serum albumin. The radioactivity of the supernatent, of the washing liquors and of the sediment was then measured. Each test was repeated three times. The tests were also effected with unlabelled $II_c$ or B-$II_b$ fragments or with unlabelled toxin. In this case, a fixed amount of labelled protein was incubed with increasing amounts of unlabelled proteins.

It was ascertained that binding of the $^{125}$I-labelled $II_c$ fragment was increasing linearly with the membrane concentration.

Displacement of the $^{125}$I-$II_c$ fragment bound to the isolated synaptic membranes by the unlabelled $II_c$ fragment or labelled tetanus toxin and displacement of the non $^{125}$I-labelled tetanus toxin by the unlabelled $II_c$ or B-$II_b$ fragments were measured. The results obtained are shown in FIGS. 2A and 2B wherein there was plotted as ordinates the specific binding of the $^{125}$I-$II_c$ fragment (FIG. 2A) as expressed in cpm (counts per minute) or of the $^{125}$I-labelled tetanus toxin (FIG. 2B) and as abscissae the molar concentration (M) of $II_c$, B-$II_b$ fragments or of tetanic toxin.

The half maximal displacements were computed from the curves in FIGS. 2A and 2B and are gathered in table I.

The results in table I show that the half maximal displacement of the $^{125}$I-$II_c$ fragment bound to synaptic membranes has approximately the same value whether it is caused by the unlabelled $II_c$ fragment or by the whole tetanus toxin. The results in table I also show that the unlabelled $II_c$ fragment is as much effective to displace $^{125}$I-labelled tetanus toxin as the unlabelled toxin is to displace the $^{125}$I-$II_c$ fragment.

In contrary, the B-$II_b$ fragment is twice more effective than the $II_c$ fragment to displace the 125 iodine-labelled tetanus toxin bound to synaptic membranes.

The Hill transformation of the displacement of the $^{125}$I-$II_c$ fragment bound to isolated synaptic membranes by the unlabelled $II_c$ fragment, expressed as $$\mathrm{Log}_{10}\frac{\%\ B\ \mathrm{max}}{100\% - \%\ B\ \mathrm{max}}\ /\mathrm{Log}_{10}$$

of the concentration of the unlabelled $II_c$ fragment provides a linear curve (FIG. 3) with a slope of 1.68 which may be construed as showing a positive cooperativity according to Cornish-Bowden et al., Diagnostic uses of the Hill (Logit and Nernst) plots. J. Mol. Biol. 95 (1975) 201–212.

The same tests as above were effected with the thiolated $II_c$ fragment according to the invention obtained according to the above Example I. The results obtained, also shown in table I, show that thiolation of the $II_c$ fragment according to the invention does not substantially modify the properties of fragment $II_c$ to be bound to syna